(12) United States Patent
Joko

(10) Patent No.: US 8,129,115 B2
(45) Date of Patent: Mar. 6, 2012

(54) METHOD OF MODIFYING NUCLEOTIDE CHAIN

(75) Inventor: Shigeki Joko, Ehime (JP)

(73) Assignee: Panasonic Corporation, Osaka (JP)

( * ) Notice: Subject to any disclaimer, the term of this patent is extended or adjusted under 35 U.S.C. 154(b) by 513 days.

(21) Appl. No.: 12/303,313

(22) PCT Filed: Jun. 4, 2007

(86) PCT No.: PCT/JP2007/061309
§ 371 (c)(1),
(2), (4) Date: Dec. 3, 2008

(87) PCT Pub. No.: WO2007/142202
PCT Pub. Date: Dec. 13, 2007

(65) Prior Publication Data
US 2010/0015670 A1    Jan. 21, 2010

(30) Foreign Application Priority Data
Jun. 6, 2006    (JP) .................. 2006-156731

(51) Int. Cl.
*C12Q 1/68*    (2006.01)
*C12P 19/34*    (2006.01)

(52) U.S. Cl. ........................... 435/6.1; 435/91.2

(58) Field of Classification Search ................ None
See application file for complete search history.

(56) References Cited

U.S. PATENT DOCUMENTS

| 4,711,955 A | 12/1987 | Ward et al. .............. 536/29 |
| 2006/0147916 A1* | 7/2006 | Ishibashi et al. .......... 435/6 |
| 2007/0218478 A1* | 9/2007 | Bai et al. .............. 435/6 |

FOREIGN PATENT DOCUMENTS

| DE | 198 12 103 | 9/1999 |
| EP | 1 647 592 | 4/2006 |
| JP | 58-62600 | 4/1983 |
| JP | 5-331185 | 12/1993 |
| JP | 2003 246794 | 9/2003 |
| JP | 2003-246794 | 9/2003 |
| WO | WO99/47536 | 9/1999 |
| WO | WO 00/55363 | 9/2000 |

OTHER PUBLICATIONS

Chang, L.M. et al, "Multiple Roles of Divalent Cation in the Terminal Deoxynucleotidyltransferase Reaction," Journal of Biological Chemistry, vol. 265, No. 29, 1990, pp. 17436-17440.

* cited by examiner

*Primary Examiner* — Ardin Marschel
*Assistant Examiner* — Channing S Mahatan
(74) *Attorney, Agent, or Firm* — Steptoe & Johnson LLP

(57) ABSTRACT

A nucleotide chain to be modified, a nucleotide having a particular base that is different from bases constituting the nucleotide chain, an enzyme catalyzing addition of the nucleotide to the 3'-terminus of the nucleotide chain, a degrading enzyme acting specifically on the nucleotide, and a desired modifier for modifying the nucleotide chain are allowed to coexist in a buffer solution as a mixture solution such that: the nucleotide is added to the 3'-terminus of the nucleotide chain; the sequence of the added nucleotide is degraded to form, at the 3'-terminus of the nucleotide chain, a functional group capable of binding to the modifier; and the 3'-terminus of the nucleotide chain having the functional group thus formed is directly modified with the modifier. The reactions at three stages continuously proceed in the mixture solution. As a result, simplified procedures and reduced reaction time can be achieved.

7 Claims, 6 Drawing Sheets

METHOD OF MODIFYING NUCLEOTIDE CHAIN

The present application is based on International Application PCT/JP2007/061309 filed Jun. 4, 2007, which claims priority to Japanese Patent Application No. 2006-156731, filed Jun. 6, 2006, the entire contents of which are hereby incorporated by reference.

TECHNICAL FIELD

The present invention relates to a method of modifying a nucleotide chain. Particularly, the present invention relates to a method of directly modifying the 3'-terminus of a nucleotide chain with a modifier for labeling or immobilizing the nucleotide chain.

BACKGROUND ART

In gene analysis, radioisotopes have heretofore been used as a modifier for labeling a nucleotide chain such as DNA, RNA, oligonucleotides, or nucleic acids. However, these radioisotopes have a limited duration attributed to half-life, the limited number of handling facilities, radiation exposure, difficulty of discarding, etc. Therefore, the use thereof is on a downward trend. In recent years, modifiers such as fluorescent materials (e.g., fluorescein) and biotin have been used generally as a substitute for the radioisotopes.

Methods of modifying the 5'-terminus of a nucleotide chain via the phosphate group have been proposed. These methods involve modifying the 5'-terminus of the nucleotide chain with a modifier through a chemical cross-linking condensation reaction using the 5'-terminal phosphate group as a functional group (e.g., Non-Patent Documents 1 to 2 (listed later; the same holds true for the description below). Alternatively, methods of modifying a nucleotide chain during chemical synthesis thereof have also been proposed. These methods involve introducing a phosphate group labeled with a modifier into the nucleotide chain during the chemical synthesis (e.g., Patent Documents 1 to 4 and Non-Patent Documents 3 to 4). The methods can also be applied to the automatic chemical synthesis of nucleotide chains and have therefore been used frequently.

However, the methods of modifying the 5'-terminus are capable of modifying one nucleotide chain molecule with only one modifier and also require a long time for the cross-linking condensation reaction. The methods of modifying a nucleotide chain during the chemical synthesis thereof allow for chemical synthesis of allegedly up to 130 nucleotides. The synthesis method thereof adds and polymerizes the nucleotides one by one and has addition/polymerization efficiency of up to 99% in a single run. Therefore, the synthesis of a larger number of nucleotides results in lower synthesis yields. To acquire sufficient yields, the number of nucleotides must be limited (e.g., Non-Patent Document 5). Furthermore, a color or luminescent reaction using alkaline phosphatase has been used frequently in gene detection by virtue of the high sensitivity thereof (e.g., Non-Patent Documents 6 to 7). However, the alkaline phosphatase has the property of dephosphorylating the 5'-terminus of the nucleotide chain. Therefore, the modifier is dissociated from the nucleotide chain. Thus, the alkaline phosphatase cannot be used for the nucleotide chain having the modified 5'-terminus.

In addition to the methods of modifying the 5'-terminus, methods using a replication or transcription reaction have also been proposed. These methods involve incorporating a nucleotide modified in advance with a modifier into a nucleotide chain through the replication or transcription reaction to obtain the nucleotide chain modified with the modifier. The replication reaction is performed by, for example, nick translation, random primer, and primer extension methods previously used in radioisotope labeling. In this case, deoxyribonucleotide 5'-triphosphate modified in advance with a modifier instead of radioisotopes is incorporated into the nucleotide chain using the replication reaction catalyzed by DNA polymerase. Alternatively, ribonucleotide 5'-triphosphate modified in advance with a modifier is incorporated into the nucleotide chain using the transcription reaction catalyzed by RNA polymerase (e.g., Patent Documents 5 to 8 and Non-Patent Documents 6 and 8 to 9). These modification methods advantageously have simplified procedures, a high amount of nucleotide chain modification, modifier stability, and the lack of modifier dissociation caused by alkaline phosphatase and have therefore been used frequently as a method suitable for gene analysis. Furthermore, these modification methods can be used in combination with a polymerase chain reaction (PCR) or RNA amplification reaction to simultaneously achieve gene amplification and labeling reactions (e.g., Non-Patent Documents 10 to 12). Therefore, these methods have been used frequently in comprehensive gene analysis typified by DNA microarrays (e.g., Patent Documents 9 to 10 and Non-Patent Documents 13 to 15).

However, the modification methods using a replication or transcription reaction are based on the incorporation of a nucleotide modified in advance with a modifier, that is, an artificial nucleotide. This artificial nucleotide is inferior in incorporation efficiency to original nucleotides and is also inferior in amplification efficiency to the original nucleotides, even when used in combination with PCR (e.g., Patent Document 8 and Non-Patent Document 16). In addition, the amount of modifiers incorporated is as variable as 12 to 25 molecules per nucleotide chain molecule (e.g., Non-Patent Document 17), leading to unfavorable reproducibility of the amount of modification. Moreover, the modifier incorporated into the nucleotide chain inevitably causes steric hindrance during hybridization, that is, formation of a nucleotide chain duplex, in gene analysis. Furthermore, the synthesis of the nucleotide modified in advance with a modifier is complicated. Not everyone can easily synthesize such a nucleotide (e.g., Non-Patent Documents 8 and 18). As a result, the type of the modifier that can be used is limited.

Other modification methods have also been proposed, which do not require a nucleotide chain serving as a template as required in the modification methods using a replication or transcription reaction. These methods can modify a nucleotide chain through an addition reaction of a nucleotide in the absence of the template. Examples of the methods include: a method of tailing, using terminal deoxynucleotidyl transferase, the 3'-terminus of a nucleotide chain with deoxyribonucleotide 5'-triphosphate or dideoxyribonucleotide 5'-triphosphate modified in advance with a modifier (e.g., Non-Patent Documents 19 to 21); and a method of tailing, using RNA ligase, a nucleotide chain with deoxyribonucleotide-3',5'-bisphosphate or ribonucleotide-3',5'-bisphosphate modified in advance with a modifier (e.g., Patent Document 11 and Non-Patent Document 22). Among them, the method of tailing with dideoxyribonucleotide 5'-triphosphate or the method of tailing with ribonucleotide-3',5'-bisphosphate is capable of modifying one nucleotide chain molecule with only one modifier molecule. By contrast, the method of tailing with deoxyribonucleotide 5'-triphosphate modified in advance with a modifier is capable of modifying one nucleotide chain molecule with plural modifier molecules.

However, such a method of tailing with deoxyribonucleotide 5'-triphosphate modified in advance with a modifier varies in the number of the modified nucleotides added depending on reaction conditions and disadvantageously forms an unnecessary nucleotide sequence. This unnecessary nucleotide sequence is also responsible for a mismatch during hybridization in gene analysis. As also described in the modification methods using a replication or transcription reaction, not everyone can easily synthesize such a nucleotide modified in advance with a modifier. As a result, the type of the modifier that can be used is limited.

A modifier can be introduced into the 3'-terminus of a nucleotide chain not only by the tailing but by chemical synthesis. In the latter case, an unnecessary nucleotide sequence is not formed. However, the unfavorable yields and constraints of a nucleotide chain length already described in the modification methods using chemical synthesis cannot be circumvented.

Nucleotide chain modification is performed not only for labeling but for immobilizing the nucleotide chain onto a substrate. The substrate previously used for immobilization is, for example, a nitrocellulose, nylon, or polyvinylidene fluoride substrate processed to have hydrophobicity and positive charge. In this case, the nucleotide chain is immobilized onto the substrate through a hydrophobic bond between the nucleotide chain and the substrate or through an electrostatic bond between the negatively charged phosphate group of the nucleotide chain and the positively charged substrate.

In this immobilization method, a longer nucleotide chain length results in higher substrate occupancy per nucleotide chain molecule. Therefore, the amount of nucleotide chains immobilized per substrate unit area is reduced. Moreover, the nucleotide chain immobilized on the substrate is disadvantageously dissociated therefrom. To solve these problems, methods have been used, which involve: modifying the terminus of a nucleotide chain with a modifier having a functional group, while forming a binding group for the functional group on a substrate surface; and cross-linking and condensing the functional group in the modifier with the binding group on the substrate surface to immobilize the nucleotide chain onto the substrate surface through a covalent bond (e.g., Patent Documents 12 to 15 and Non-Patent Document 23). These methods can achieve more stable and more firm immobilization of the nucleotide chain than that through the conventional hydrophobic and electrostatic bonds. Examples of functional group-binding group combinations used include amino-carboxyl, amino-isothiocyanate, amino-aldehyde, amino-succinimide, and amino-epoxy groups.

However, the 5'-terminus of the nucleotide chain is modified via the phosphate group with the modifier having a functional group. As described above, such modification via the phosphate group has disadvantages. Specifically, the nucleotide chain is dissociated therefrom by phosphatase. Accordingly, the nucleotide chain thus modified cannot be used in detection through a luminescent reaction. Alternatively, the 3'-terminus of the nucleotide chain is also modified with the modifier having a functional group. In such a case, the constraints of a nucleotide chain length cannot be circumvented for acquiring sufficient yields that can be synthesized chemically.

To solve these problems associated with nucleotide chain labeling or immobilization, a method of directly modifying the 3'-terminus of a nucleotide chain with a modifier has been proposed (see Patent Document 16). In this method, two or more nucleotides having an uracil base are added to the 3'-terminus of the nucleotide chain; the added nucleotide is degraded with uracil-DNA glycosidase to form an aldehyde group at the 3'-terminus; and the 3'-terminus of the nucleotide chain is directly modified with a modifier having an amino group through a covalent bond between the aldehyde group and the amino group.

PATENT DOCUMENTS

1: Japanese Patent No. 1651975
2: Japanese Patent No. 1706289
3: Japanese Patent No. 1780550
4: Japanese Patent No. 1845794
5: Japanese Patent No. 1972288
6: Japanese Patent No. 2131226
7: Japanese Patent No. 2625095
8: Japanese Patent Laid-Open No. 61-115094
9: Japanese Patent No. 3272365
10: National Publication of International Patent Application No. 2002-538836
11: Japanese Patent Laid-Open No. 5-331185
12: Japanese Patent Laid-Open No. 2000-63154
13: Japanese Patent Laid-Open No. 2001-66304
14: Japanese Patent Laid-Open No. 2003-161731
15: National Publication of International Patent Application No. 2003-526078
16: Japanese Patent Laid-Open No. 2003-246794

NON-PATENT DOCUMENTS

1: Chu B. C. F et al., Nucleic Acids Res., vol. 11, p. 6513, 1983
2: Chollet A. et al., Nucleic Acids Res., vol. 13, p. 1529, 1985
3: Alves A. M. et al., Tetrahedron Letters, vol. 30, p. 3089, 1989
4: Cocuzza A. J., Tetrahedron Letters, vol. 30, p. 6287, 1989
5: Custom Oligonucleotide Synthesis in Sigma Aldrich website; Japan Patent Office website, Shiryou shitsu (Archives (in English; the same holds true for the description below)), Sonota no sankou jouhou (Other References), Hyoujun gijutsushu (Database of Standard Techniques), Kakusan no zouhuku oyobi kenshutsu (Nucleic Acid Amplification and Detection), 1-1 purobu/puraima to shite tekishita hairetsu no sentaku houhou (Method of Selecting Sequences Suitable for Probes/Primers).
6: Leary J. J. et al., Proc. Natl. Acad. Sci. USA, vol. 80, p. 4045, 1983
7: Bronstein I. et al., Methods Enzymol., vol. 217, p. 398, 1993
8: Langer P. R. et al., Proc. Natl. Acad. Sci. USA, vol. 78, p. 6633, 1981
9: Murasugi A. et al., DNA, vol. 3, p. 269, 1984
10: Van Gelder R. N. et al., Proc. Natl. Acad. Sci. USA, vol. 87, p. 1663, 1990
11: Reid T. et al., Proc. Natl. Acad. Sci. USA, vol. 89, p. 1388, 1992
12: Baugh L. R. et al., Nucleic Acids Res., vol. 29, p. e29, 2001
13: Schena M. et al., Science, vol. 270, p. 467, 1995
14: Shalon D. et al., Genome Res., vol. 6, p. 639, 1996
15: Chipping Forecast, Nature Genet., vol. 21 Supplement, January 1999
16: Yu H. et al., Nucleic Acids Res., vol. 22, p. 3226, 1994
17: Microarray Handbook in GE Healthcare Bio-Sciences website.
18: Dale R. M. K et al., Biochemistry, vol. 14, p. 2447, 1975
19: Riley L. K. et al., DNA, vol. 5, p. 337, 1986
20: Trainor G. L. et al., Nucleic Acids Res., vol. 16, p. 11846, 1988

21: Schmitz G. G. et al., Anal. Biochem., vol. 192, p. 222, 1991
22: Richardson R. W. et al., Nucleic Acids Res., vol. 11, 1983
23: Guo Z. et al., Nucleic Acids Res., vol. 22, p. 5456, 1994

DISCLOSURE OF THE INVENTION

As described above, various methods of modifying a nucleotide chain have been proposed. However, each of these methods has both advantages and disadvantages. Thus, users bear the burden of inevitably sorting out the modification methods according to applications. In brief, methods of modifying the 5'-terminus of a nucleotide chain via the phosphate group have unfavorable stability. Methods of modifying the 5'- or 3'-terminus of a nucleotide chain during chemical synthesis thereof have constraints of a nucleotide chain length and unfavorable yields. Methods using a replication or transcription reaction have, from the outset, a limited use to nucleotide chain labeling with a modifier such as fluorescent materials and also have unfavorable replication or transcription efficiency. A tailing method of adding a nucleotide modified in advance with a modifier disadvantageously forms an unnecessary nucleotide sequence. For immobilizing a nucleotide chain onto a substrate, the nucleotide chain is preferably modified with a modifier having a functional group capable of covalently binding to a binding group on the substrate surface. These problems cannot be evaded for the modification.

A method described in Patent Document 10 can directly modify the 3'-terminus of a nucleotide chain with any modifier, regardless of a nucleotide chain length. However, among addition, degradation, and modification reactions, reaction conditions must be changed, and samples must be collected by ethanol precipitation or other methods. Thus, this method requires 10 hours or longer for completing the reactions.

To solve these problems, an object of the present invention is to directly modify the 3'-terminus of a nucleotide chain with a modifier in a reduced reaction time under reaction conditions minimally changed among stages.

To attain the object, a method of modifying a nucleotide chain according to the present invention includes allowing a nucleotide chain to be modified, a nucleotide having a particular base that is different from bases constituting the nucleotide chain, an enzyme catalyzing addition of the nucleotide to the 3'-terminus of the nucleotide chain, a degradation enzyme acting specifically on the added nucleotide having a particular base, and a desired modifier for modifying the nucleotide chain to coexist in a buffer solution as a reaction mixture solution such that: the nucleotide having a particular base is added to the 3'-terminus of the nucleotide chain; the sequence of the added nucleotide is degraded to form, at the 3'-terminus of the nucleotide chain, a functional group capable of binding to the modifier; and the 3'-terminus of the nucleotide chain having the functional group thus formed is directly modified with the modifier. The nucleotide chain is directly modified with the modifier through a series of reactions without separating reaction products, etc. in the mixture solution during the reactions. Thus, simplified procedures and reduced reaction time can be achieved. Moreover, the method of modifying a nucleotide chain according to the present invention is independent of a nucleotide chain length and is therefore highly convenient.

The nucleotide chain to be modified, the nucleotide, the modifier, and both the enzymes may be mixed initially to simultaneously cause addition, degradation, and modification reactions; or otherwise, the nucleotide chain to be modified, the nucleotide, and both the enzymes may be mixed to simultaneously cause addition and degradation reactions. In the latter case, a modification reaction is caused by adding the modifier to the mixture solution after the degradation reaction.

In the method of modifying a nucleotide chain according to the present invention, an activator which does not inhibit the modification reaction of the modifier is added to the reaction mixture solution as an activator for activating the enzyme catalyzing the addition reaction. This is because the reaction mixture solution thus obtained preferably has composition free from a reaction inhibitor of the reactions at three stages.

In the method of modifying a nucleotide chain according to the present invention, the reaction mixture solution further contains a buffer component which moderates reaction activity of the enzyme catalyzing the addition reaction. This is because the degradation reaction through which the sequence of the added nucleotide is degraded is facilitated by preventing the nucleotide having a particular base from being excessively added to the 3'-terminus of the nucleotide chain.

In the method of modifying a nucleotide chain according to the present invention, when the enzyme catalyzing the addition reaction is terminal deoxynucleotidyl transferase, a divalent metal cation other than a cobalt ion can be used as the activator. This is because the divalent metal cation other than a cobalt ion can prevent precipitation with a modifier having an amino group. A manganese or magnesium ion can be used preferably.

In the method of modifying a nucleotide chain according to the present invention, when the enzyme catalyzing the addition reaction is terminal deoxynucleotidyl transferase, 4-(2-hydroxyethyl)piperazine-1-ethanesulfonic acid, 2-morpholinoethanesulfonic acid, or 3,3-dimethylglutaric acid can be used preferably as the buffer component.

In the method of modifying a nucleotide chain according to the present invention, the particular base in the nucleotide to be added is a base which is absent in nucleotides constituting original (natural) nucleotide chains. Specifically, the particular base is not selected from among adenine, guanine, cytosine, and thymine and may be a variant base formed through alkylation, deamination, halogenation, hydroxylation, or oxidation of these bases. The nucleotide chain to be modified, when tailed with the nucleotide having such a particular base, can maintain the initial state even by the action of a degrading enzyme specific thereto.

In the method of modifying a nucleotide chain according to the present invention, DNA glycosylase or a DNA repair enzyme can be used as the degrading enzyme. Such a degrading enzyme causes, in the sequence of the added nucleotide, base elimination, deoxyribose ring opening, and 3'-phosphate group dissociation. As a result, an aldehyde group is formed at the 3'-terminus of the nucleotide chain. When the nucleotide to be added is 2'-deoxyuridine 5'-monophosphate, uracil-DNA glycosylase can be used preferably as the degradation enzyme.

In the method of modifying a nucleotide chain according to the present invention, the modifier may have $—NH_2$. This is because the $—NH_2$ moiety present in the modifier is cross-linked spontaneously with the functional group such as an aldehyde group without the use of any particular catalytic reaction. For example, a Schiff base is formed between aldehyde and $—NH_2$.

In the method of modifying a nucleotide chain according to the present invention, the modifier may be a substance for labeling and/or conjugating the nucleotide chain. Such a modifier may be a fluorescent substance, a vitamin, a lipid, an amino acid, an oligopeptide, a protein, or an exogenous substance.

In the method of modifying a nucleotide chain according to the present invention, the modifier may be a substance via which the nucleotide chain is bound to a substrate. Such a modifier may be a compound having amino and thiol groups. Alternatively, the modifier may be a compound which has an amino group and has an alkoxysilyl group hydrolyzable to a silanol group.

Specifically, in the method of modifying a nucleotide chain according to the present invention, a nucleotide chain having any base sequence can be mixed with: the nucleotide having a particular base; the enzyme catalyzing the nucleotide addition to the 3'-terminus of the nucleotide chain; DNA glycosylase or a DNA repair enzyme as the degradation enzyme acting on the added nucleotide having a particular base; and the modifier capable of binding to an aldehyde group formed at the 3'-terminus of the nucleotide chain through degradation, by the degrading enzyme, of the nucleotide added by the enzyme.

In the method of modifying a nucleotide chain according to the present invention, a buffer solution containing a nucleotide chain having any base sequence can be mixed with 2'-deoxyuridine 5'-triphosphate, terminal deoxynucleotidyl transferase and an activator thereof, and uracil-DNA glycosylase, and this reaction mixture solution can be heat-treated or alkali-treated and then mixed with a modifier having HUT-group.

According to the method of modifying a nucleotide chain according to the present invention, a nucleotide chain can be modified with a desired modifier conveniently in a short time, with the original state of the nucleotide chain maintained, that is, without adding excess nucleotides thereto. Thus, the method of modifying a nucleotide chain according to the present invention is independent of the number of strands (single or double) of a nucleotide chain.

BEST MODE FOR CARRYING OUT THE INVENTION

Hereinafter, embodiments of the present invention will be described with reference to the drawings.

Figure 1:
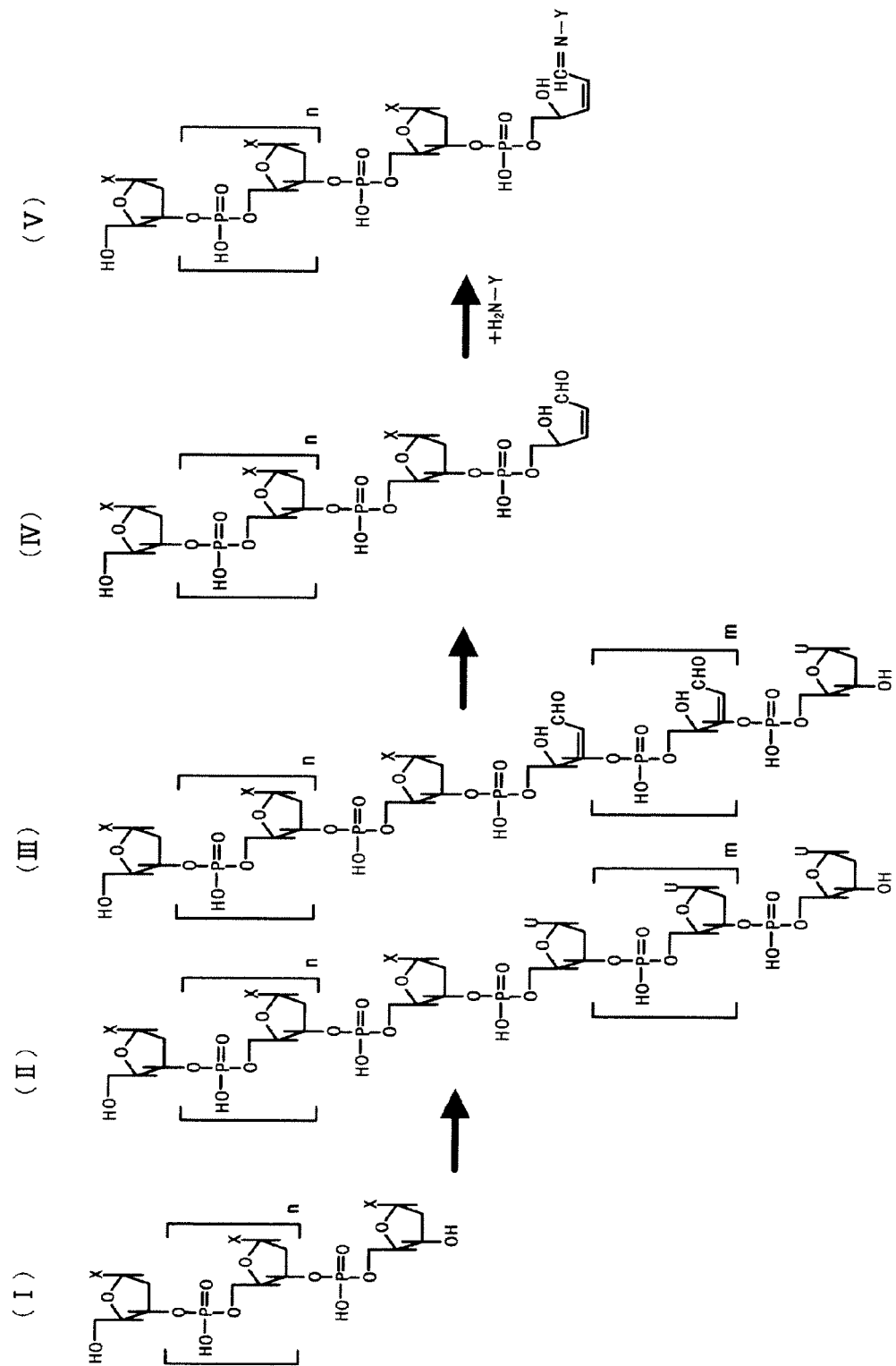
FIG. 1 is a schematic reaction scheme showing the principle of a method of modifying a nucleotide chain according to the present invention.

First, the principle of a method of modifying a nucleotide chain according to the present invention will be described with reference to FIG. 1. In the drawing, X represents any base selected from among adenine, guanine, thymine, and cytosine; U represents a uracil base; n represents any natural number; and m represents 0 or any natural number.

A buffer solution containing a nucleotide chain (I) having any base sequence is mixed with 2'-deoxyuridine 5'-triphosphate (hereinafter, abbreviated to dUTP) represented by the following formula:

[Formula 1]

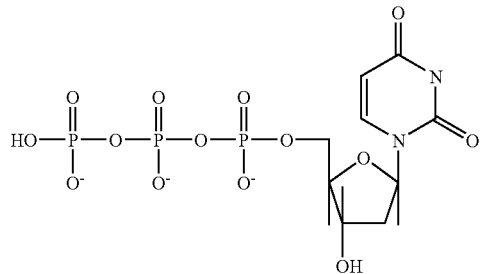

terminal deoxynucleotidyl transferase (hereinafter, abbreviated to TdT), uracil-DNA glycosylase (hereinafter, abbreviated to UDG), and an activator for activating TdT. The activator that can be used preferably is a divalent metal cation such as a magnesium or manganese ion.

As a result, by the polymerase action of the TdT, the 3'-terminus of the nucleotide chain (I) is tailed, linearly and consecutively, with at least two 2'-deoxyuridine 5'-monophosphates (hereinafter, abbreviated to dUMPs) represented by the following formula:

[Formula 2]

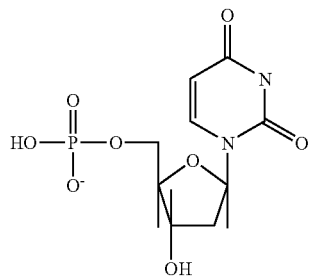

to form a nucleotide chain (II). At the same time, by the action of the UDG, the uracil base of the dUMP in the tail is dissociated therefrom, while the glycosidic bond of the deoxyribose is hydrolyzed to form a nucleotide chain (III) having an aldehyde group. The coexistence of the enzymes TdT and UDG enables shift immediately to the degradation reaction: the nucleotide chain can be tailed with dUMPs by the TdT, while the dUMPs in the tail can be degraded by the UDG.

Next, the liquid reaction mixture containing the nucleotide chain (III) thus formed is heat-treated at 90 to 100° C. for 5 to 15 minutes or alkali-treated by adding dropwise a strong alkaline solution such as a sodium hydroxide or potassium hydroxide solution to the liquid reaction mixture. As a result, the degraded tail is dissociated therefrom to obtain a nucleotide chain (IV) in which an aldehyde group is directly formed at the 3'-terminus of the nucleotide chain (I) as a starting material.

Finally, the liquid reaction mixture containing the nucleotide chain (IV) is mixed with a modifier having $H_2N$— (in the drawing, Y represents the remainder of a compound, molecule, or substance constituting the modifier). As a result, the —$NH_2$ moiety present in the modifier is cross-linked spontaneously with the aldehyde group formed at the 3'-terminus of the nucleotide chain without any particular catalytic reaction to form a Schiff base between the —$NH_2$ moiety and the aldehyde group. The nucleotide chain (V) thus obtained has the 3'-terminus directly modified with the modifier and is free from excess nucleotides.

A cobalt ion has heretofore been used frequently as the activator for TdT. However, the cobalt ion is observed to form insoluble pellets with such a modifier having —NH$_2$ for modifying the nucleotide chain. Therefore, preferably, the use of the cobalt ion is avoided in the present invention.

The magnesium or manganese ion used preferably as an activator for TdT in the present invention forms no insoluble pellets with the modifier. The magnesium or manganese ion has a lower ability to activate the enzyme than that of the cobalt ion. The use of such an ion can rather limit the amount of TdT-catalyzed tailing with dUMPs and can therefore facilitate the reaction by UDG using, as a substrate, the dUMPs in the tail of the nucleotide chain. Specifically, the substrate can be digested rapidly by the UDG. The nucleotide chain to be modified is tailed with at least two dUMPs linearly and consecutively, as described above. These dUMPs in the tail can act as a substrate for the uracil-DNA glycosylase.

In this way, the 3'-terminus of the nucleotide chain can be modified directly with the modifier through a series of reactions without separating components or reaction products in the liquid reaction mixture. Thus, simplified procedures and reduced reaction time can be achieved.

The method of modifying a nucleotide chain according to the present invention is free from incorporation of a modifier into a nucleotide chain using a replication or transcription reaction as performed in conventional methods. Therefore, unlike the incorporation reaction, the amount of modification with the modifier is independent of a nucleotide chain length. Moreover, the method of modifying a nucleotide chain according to the present invention requires a much shorter modification time than that required for methods of modifying a 5'-terminus through a cross-linking condensation reaction (e.g., Nucleic Acids Res., vol. 13, p. 1529, 1985). Furthermore, the method of modifying a nucleotide chain according to the present invention can circumvent constraints of a nucleotide chain length, that is, the limited number of nucleotides (synthesis yields), which obstruct methods of modifying the 5'-terminus of a nucleotide chain simultaneously with chemical synthesis thereof. From these points of view, the method of modifying a nucleotide chain according to the present invention is useful in, for example, gene analysis that requires nucleotide chain labeling, immobilization, etc.

The modifier is absent in the main chain (portion except for the 3'-terminus) of the nucleotide chain. Therefore, the modifier, in gene analysis, can be prevented from causing steric hindrance even during formation of a duplex between the modified nucleotide chain and a target nucleotide chain thereof.

When the nucleotide chain of interest is several tens of nucleotides in length that can be synthesized chemically, a nucleotide chain having a sequence with the particular base may be synthesized in advance. In this case, the reaction at the first stage (nucleotide chain (I)→nucleotide chain (II)) can be omitted.

Figure 2:
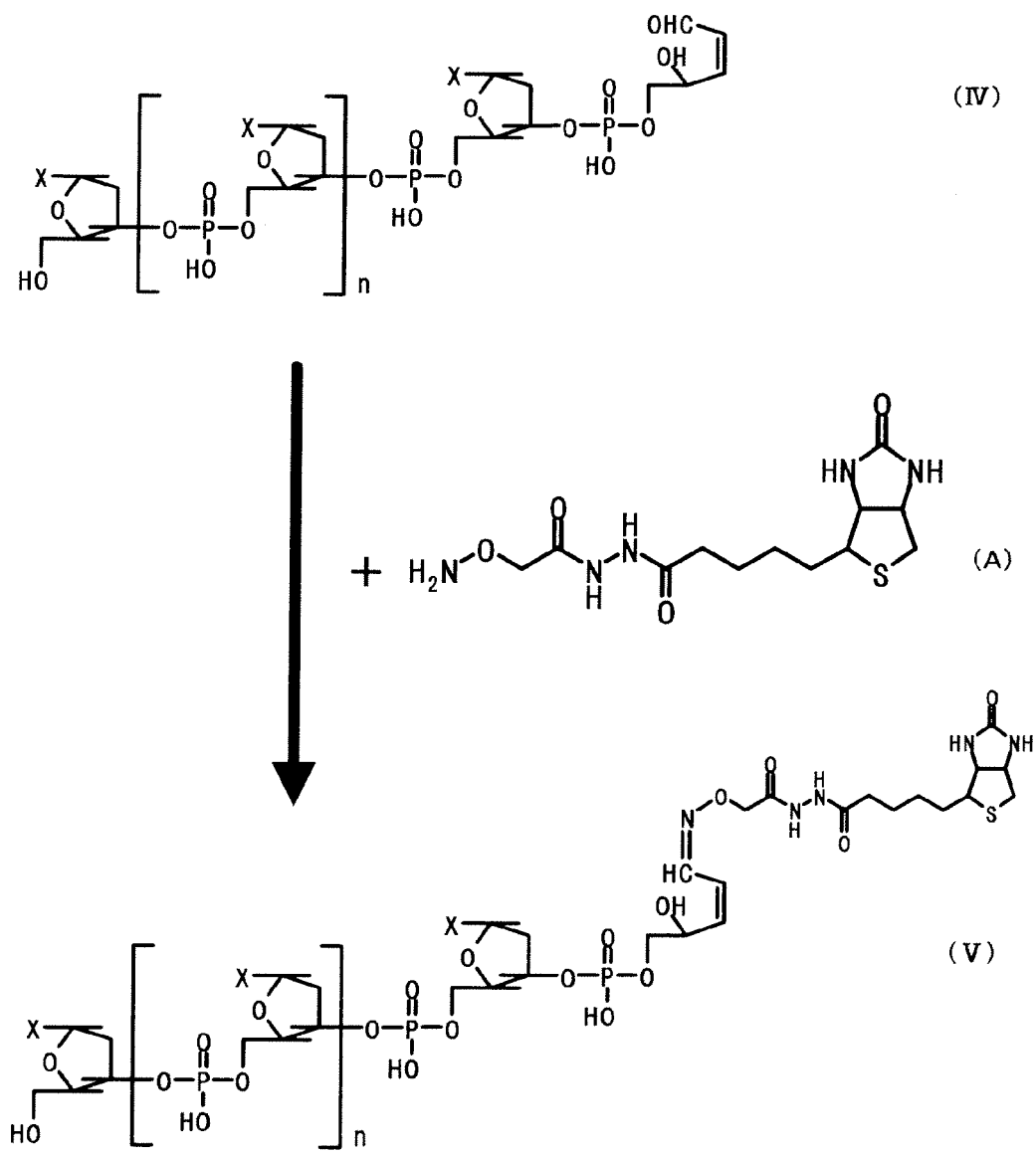
FIG. 2 is a schematic reaction scheme showing a process of labeling the nucleotide chain using the reactions of FIG. 1.

For nucleotide chain labeling, the nucleotide chain (IV) is reacted, for example, as shown in FIG. 2, with N-aminooxymethylcarbonylhydrazino-D-biotin (A) (hereinafter, abbreviated to aminooxy biotin) wherein an aminooxy group is formed at the terminus of biotin used frequently as a modifier. The nucleotide chain (V) thus obtained can have the 3'-terminus directly bound with biotin. Such a nucleotide chain labeled with biotin can be used preferably as a probe or target for gene analysis such as hybridization.

Figure 3:
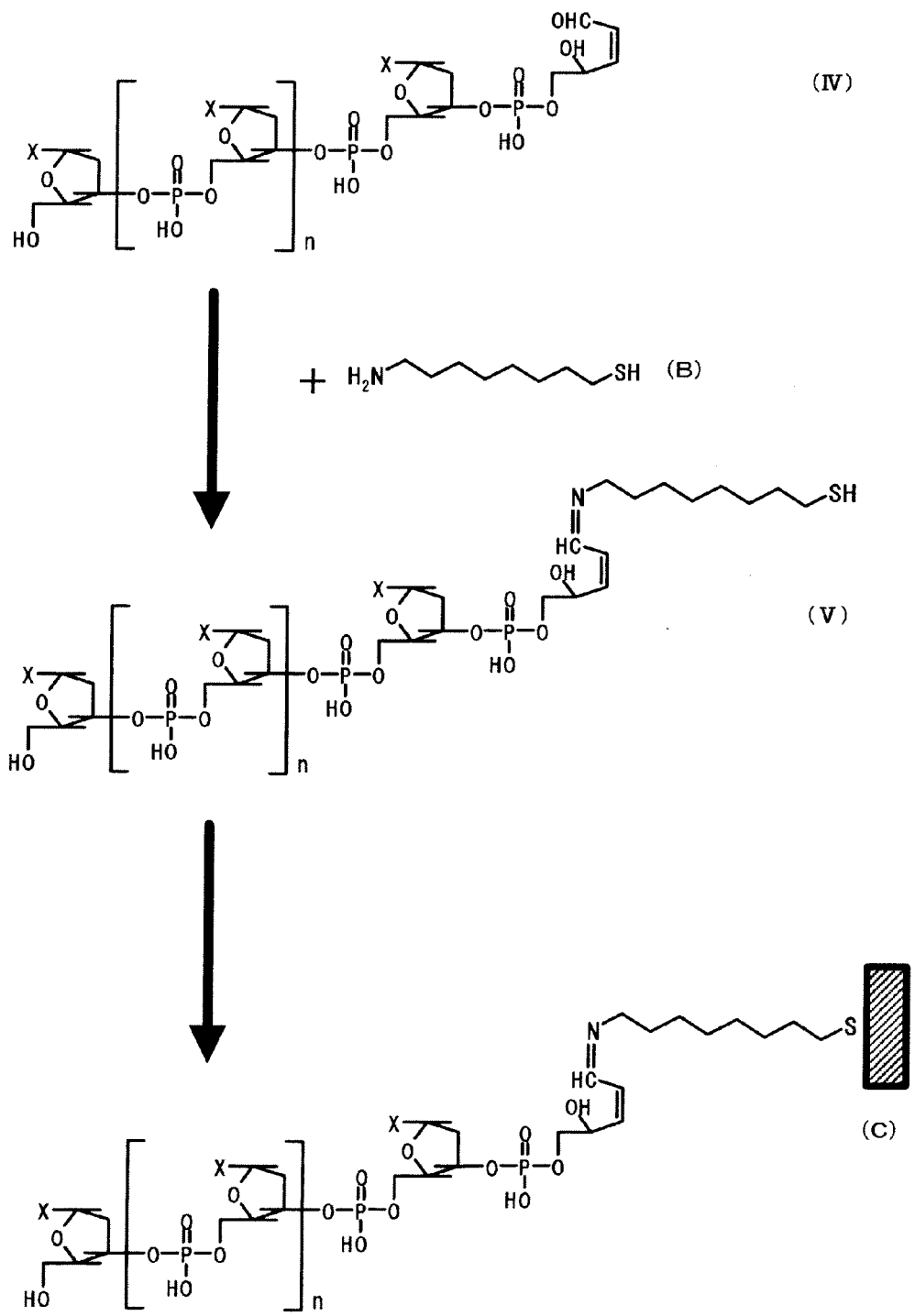
FIG. 3 is a schematic reaction scheme showing a process of immobilizing the nucleotide chain onto a noble metal substrate using the reactions of FIG. 1.

For nucleotide chain immobilization, the nucleotide chain (IV) having an aldehyde group at the 3'-terminus is reacted, for example, as shown in FIG. 3, with thiol having an amino group, for example, 8-amino-1-octanethiol (B), to cause condensation between the aldehyde group and the amino group. The modified nucleotide chain (V) thus obtained has the 3'-terminus directly bound with 8-amino-1-octanethiol (residue).

Then, this nucleotide chain (V) having a thiol group is brought into contact with a noble metal (e.g., gold) substrate (C) by a method such as dropwise addition to form a strong covalent bond between the thiol group and the noble metal. As a result, the nucleotide chain (V) can be immobilized on the substrate (C). Measurement methods using the noble metal substrate thus prepared, such as electrochemical measurement, quartz crystal microbalance, and surface plasmon resonance, can be used in gene analysis.

When a metal (e.g., noble metal) substrate or a glass or plastic support having a thin metal film formed thereon is used, the modifier that can be used is aminoalkanethiol such as 8-amino-1-octanethiol, which has a thiol group capable of binding to the metal substrate or thin metal film and also has —NH$_2$ capable of binding to the nucleotide chain.

Alternatively, when a glass substrate is used, the modifier that can be used is a silane coupling compound such as gamma-aminopropyltriethoxysilane, which has an alkoxysilyl (e.g., methoxysilyl or ethoxysilyl) group hydrolyzable to a silanol group capable of binding to the glass and also has —NH$_2$ capable of binding to the nucleotide chain.

The method of modifying a nucleotide chain according to the present invention has been described by taking, as an example, tailing with dUMPs having a uracil base and degradation by the action of UDG. Alternatively, nucleotides having a base formed through a variation such as alkylation, deamination, halogenation, hydroxylation, or oxidation of adenine, guanine, cytosine, or thymine contained in natural nucleotide chains may be used, as listed in Table 1 shown below. Such a variant base is absent in the natural nucleotide chains. Specific examples of the nucleotides include 2'-deoxyribonucleotide 5'-monophosphates other than 2'-deoxyadenosine 5'-monophosphate, 2'-deoxycytidine 5'-monophosphate, 2'-deoxyguanosine 5'-monophosphate, and 2'-deoxythymidine 5'-monophosphate.

More specifically, the uracil is a product of cytosine deamination in which an amino group at carbon 4 is varied into a carbonyl group. Likewise, hypoxanthine is a product of adenine deamination in which amine at carbon 6 is varied into a carbonyl group; 3-methyladenine is a product of adenine methylation at nitrogen 3; and 8-oxoguanine is a product of guanine oxidation in which carbon 8 is varied into a carbonyl group (the numbering scheme for each base is based on the rules of the International Union of Pure and Applied Chemistry (IUPAC)).

Tailing with these nucleotides is combined with DNA glycosylases or DNA repair enzymes acting specifically on the nucleotides. Even during these reactions, the structure and configuration of the initial nucleotide chain before modification can be maintained. In this state, an aldehyde group can be formed at the 3'-terminus of the nucleotide chain. Thus, the 3'-terminus of the nucleotide chain can be modified directly with a modifier having a binding group (e.g., —NH$_2$ group) for the aldehyde group.

TABLE 1

| Base in nucleotide | DNA glycosylase/DNA repair enzyme applied thereto |
| --- | --- |
| uracil | uracil-DNA glycosylase |
| 5-hydroxyuracil | |
| 5,6-dihydroxyuracil | |
| 5-fluorouracil | |
| hypoxanthine | hypoxanthine-DNA glycosylase |
| 3-methyladenine | 3-methyladenine-DNA glycosylase type I |
| 3-ethyladenine | |
| 3-methyladenine | 3-methyladenine-DNA glycosylase type II |

TABLE 1-continued

| Base in nucleotide | DNA glycosylase/DNA repair enzyme applied thereto |
|---|---|
| hypoxanthine | |
| 3-methylguanine | |
| 7-methylguanine | |
| 1,N⁶-ethanoadenine | |
| 8-oxoguanine | |
| 7-ethylpurine | |
| 3-ethylpurine | |
| 7,3-diethylpurine | |
| 1-carboxyethyladenine | |
| 7-carboxyethylguanine | |
| O²-methylpyrimidine | |
| 7(2-ethoxyethyl)guanine | |
| 7(2-hydroxyethyl)guanine | |
| 7(2-chloroethyl)guanine | |
| 1,2-bis(7-guanyl)ethane | |
| 3-ethylthioethylpurine | |
| N$^{2,3}$-ethanoguanine | |
| N$^{2,3}$-ethenoguanine | |
| 5-hydroxymethyluracil | |
| 5-formyluracil | |
| 1,N⁴-ethenocytosine | |
| 1,N²-ethenoguanine | |
| 3,N²-ethenoguanine | |
| thymine glycol | endonuclease III |
| 5,6-dihydrothymine | |
| 5,6-dihydroxydihydrothymine | |
| hydroxycytosine | |
| urea | |
| 5-hydroxy-5-methylhydantoin | |
| 6-hydroxy-5,6-dihydroxy-pyrimidine | |
| 5-hydroxyuracil | |
| 5-hydroxy-6-hydrothymine | |
| 5,6-dihydrouracil | |
| uracil glycol | |
| 5-hydroxy-6-hydrouracil | |
| 8-oxoguanine | 8-oxoguanine-DNA glycosylase |
| 7,8-dihydro-8-oxoguanine | |
| 8-oxoadenine | |
| formamide guanine | |
| methylformamide guanine | |
| 7-methylguanine | formamide pyrimidine-DNA glycosylase |
| 1,6-diamino-5-formamide pyrimidine | |
| formamide guanine | |
| methylformamide guanine | |
| formamide adenine | |
| 8-oxoadenine | |
| 8-oxoguanine | |
| 7,8-dihydro-8-oxoguanine | |
| hydroxycytosine | |
| 5-hydroxyuracil | |
| aflatoxin-bound imidazole-ring-opened guanine | |
| imidazole-ring-opened N-2-aminofluorene-8-guanine | |
| 8-oxoguanine | MutY-DNA glycosylase |
| adenine/guanine mismatch | |
| 1,N⁴-ethenocytosine | mismatch uracil-DNA glycosylase |
| uracil/guanine mismatch | |
| pyrimidine dimer | pyrimidine dimer-DNA glycosylase |
| thymine/guanine mismatch | thymine-DNA glycosylase |
| guanine/guanine mismatch | |

The modifier may merely have a binding group for the functional group formed in the nucleotide chain. When the functional group is aldehyde as described above, a group having H₂N—, for example, an amino (H₂N—), hydrazino (H₂NHN—), or aminooxy (H₂NO—) group, may be used as appropriate.

The modifier that can be used for labeling is the aminooxy biotin (vitamin) as well as a fluorescent material having an aminooxy group, such as fluorescein, Texas Red, rhodamine, or cyanine dye compounds (typically, Cy3 or Cy5), or a non-fluorescent material such as digoxigenin. The nucleotide chain modified with the fluorescent material is useful in gene analysis, particularly, Fluorescence in situ Hybridization (FISH). Biotin is an example of vitamins, and digoxigenin is an example of lipids.

Amino acids, oligopeptides, and proteins may be used because these modifiers also have an amino group. Among the amino acids, phenylalanine, tryptophan, and tyrosine can be used preferable by virtue of the fluorescence thereof. Amino acids, peptides, etc. having no fluorescence may also be used by binding a labeling compound such as fluorescein to the side chains.

Peptides have side chains according to the number of constituent amino acids thereof. Thus, plural labeling compounds can be bound thereto. For example, trilysine, a linkage of three lysine residues, has three amino groups in the side chains. Therefore, this modifier can be modified optionally with a total of three labeling compounds having a carboxyl group, succinimide group, or the like.

The proteins that can be used are, for example, alkaline phosphatase, peroxidase, colored or fluorescent phycoerythrin, transferrin, hemoglobin, green fluorescent proteins, blue fluorescent proteins, and aequorin.

The modifier is not limited to these peptides (including proteins). Hydrocarbons such as alkyl, allyl, cycloalkane, aromatic compounds, and sugars having an amino group can be modified with a labeling compound and used as a modifier for modifying the nucleotide chain.

Other modifiers that can be used for modifying the nucleotide chain are exogenous substances such as fine particles typified by noble metal colloid (e.g., gold or silver colloid), magnetic fine particles, and polymer fine particles (e.g., polystyrene beads) having an amino group formed on the surface.

The modifier used for binding to a substrate may merely have a binding group for the functional group formed in the nucleotide chain and a binding group for the substrate. For example, any compound having amino and thiol groups can be used without particular limitations. Specific examples thereof include the aminoalkanethiol. The hydrocarbon residue between the amino and thiol groups may take various forms such as linear, branched, cyclo ring, open-chain allyl, and aromatic ring forms. The number of carbon atoms thereof, the position of the amino group, etc. can be changed.

A gold substrate is generally used in methods such as quartz crystal microbalance and surface plasmon resonance. The substrate is not limited to this gold substrate. In addition to gold, for example, noble metal (e.g., platinum or silver), copper, palladium, indium, nickel, iron, aluminum, and alloys thereof are used.

A silane coupling compound having an amino group may be used as the modifier. This silane coupling compound permits immobilization of the nucleotide chain onto substrates made of, for example, glass, silicon, silica, alumina, mica, and polymer resins (e.g., polystyrene, nylon, and epoxy). The obtained substrates can be applied to various gene analysis approaches known previously.

The silane coupling compound may be any compound having both amino and alkoxysilyl (e.g., methoxysilyl or ethoxysilyl) groups. Such a compound, as in the alkanethiol, can be used without particular limitations on structures, etc. The silane coupling compound that can be used is, for example, gamma-aminopropyltriethoxysilane, N-beta(aminoethyl)-gamma-aminopropylmethyldimethoxysilane, N-beta(aminoethyl)-gamma-aminopropyltrimethoxysilane, N-beta(aminoethyl)-gamma-aminopropyltriethoxysilane, or gamma-aminopropyltrimethoxysilane.

Even substances originally having no amino, aminooxy, or hydrazine group can be used, via an appropriate spacer having these binding groups, for modifying the nucleotide chain. For example, a substance having a carboxyl group can be used, via a spacer having a diamino structure such as 1,2- diaminoethane or 1,6-diaminohexane, for modifying the nucleotide chain. Furthermore, a substance having a cyano group or a substance having magnesium halide, such as a Grignard reagent, can also be used as a modifier.

Hereinafter, the present invention will be described more specifically with reference to specific Examples.

EXAMPLE 1

A single-stranded oligodeoxynucleotide of 25 nucleotides in length was chemically synthesized (this synthesis was entrusted to Sigma-Aldrich Japan K.K.) and used as a nucleotide chain to be modified. This nucleotide chain has the base sequence 5'-CTTATGATTTTTGTGTGAACCTCCC-3' which is complementary to a sequence at positions 5786 to 5810 of the base sequence of DNA encoding human skeletal muscle myosin heavy chain-1 (GenBank provided by the National Center for Biotechnology Information). A, G, T, and C represent adenine, guanine, thymine, and cytosine, respectively.

2.5 µM of the nucleotide chain, 1 u (unit)/µl TdT (manufactured by Fermentas), 0.2 u/µl UDG (manufactured by New England BioLabs Inc.), 1 mM dUTP, and 2 mM magnesium chloride (all indicated in the final concentrations) were mixed into a 50 mM 4-(2-hydroxyethyl)piperazine-1-ethanesulfonic acid-potassium hydroxide buffer solution (pH 7.2) (50 µl in total) and reacted at 37° C. for 2 hours. The liquid reaction mixture was heat-treated at 100° C. for 15 minutes. Subsequently, 2 mM aminooxy biotin (manufactured by DOJINDO LABORATORIES) was added thereto. This liquid reaction mixture was diluted to 2 µM in terms of the concentration of the nucleotide chain to be modified and then reacted at 37° C. for 1 hour. The added magnesium chloride serves as a divalent metal cation required as an activator for TdT.

Figure 4:
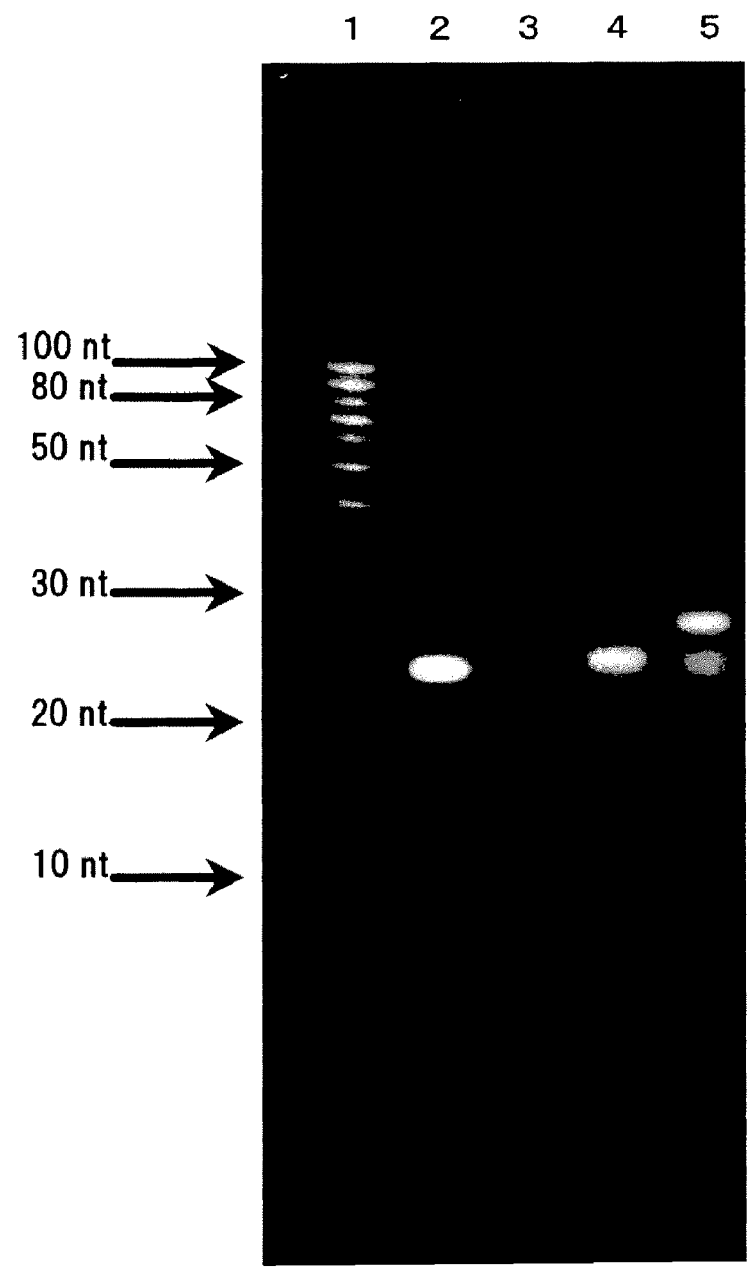
FIG. 4 is electrophoretic patterns on polyacrylamide gel showing reaction states at each stage of the method of modifying a nucleotide chain according to the present invention.

This nucleotide modification process was monitored by 7 M urea-polyacrylamide gel electrophoresis (Molecular Cloning, 2nd edition, p. 11.23, 1989). 15% polyacrylamide containing 7 M urea and 5% glycerin was used together with a buffer solution containing 89 mM Tris-boric acid and 2 mM sodium ethylenediaminetetraacetate. The nucleotide chain was detected by SYBR Gold (manufactured by Invitrogen Corp.) staining. The results are shown in FIG. 4.

A lane 1 shows an electrophoretic pattern of a molecular weight marker (manufactured by Promega Corp.); a lane 2 shows an electrophoretic pattern of an untreated nucleotide chain; a lane 3 shows an electrophoretic pattern of a nucleotide chain after the reaction at 37° C. for 2 hours; a lane 4 shows an electrophoretic pattern of a nucleotide chain after the heat treatment at 100° C. for 15 minutes; and a lane 5 shows an electrophoretic pattern of a nucleotide chain after the biotin modification treatment.

The molecular weight marker in the lane 1 contains 10-nt to 100-nt (in increments of 10 nt; 10 nt represents 10 nucleotides) nucleotide chains. The arrows in the drawing respectively represent migration positions of 100-nt, 80-nt, 50-nt, 30-nt, 20-nt, and 10-nt polynucleotide chains. The untreated nucleotide chain shown in the lane 2 is 25 nt long.

In the lane 3, the nucleotide chain is approximately 27 to 30 nt long. This demonstrates that the coexistence of TdT and UDG in the liquid reaction mixture allowed the tailing reaction of the nucleotide chain with dUMPs and the degradation reaction of the dUMPs in the tail to proceed successively.

In the lane 4, the nucleotide chain restored the length to 25 nt. This demonstrates that the dUMPs degraded by UDG were dissociated therefrom by the heat treatment.

In the lane 5, the nucleotide chain exhibited slower mobility than that of the nucleotide chains in the lanes 2 and 4. As previously reported, the electrophoretic mobility of a nucleotide chain having the 5'-terminus directly modified with biotin is slow (e.g., Chollet A. et al., Nucleic Acids Res., vol. 13, p. 1529, 1985). Thus, this result demonstrates that the nucleotide chain was modified with biotin. This is because, along with the dissociation of the dUMPs, an aldehyde group was formed at the 3'-terminus of the nucleotide chain and in turn cross-linked spontaneously with the aminooxy group without the need of any particular catalyst to form a Schiff base between the aminooxy group, a kind of —NH$_2$, and the aldehyde group. The nucleotide chain thus obtained had the 3'-terminus directly modified with biotin.

The configuration of the base sequence of the nucleotide chain, the nucleotide chain length, the type of the modifier, the reaction conditions, and the reaction composition (buffer solution, etc.) shown in Example 1 are considered as illustrative and not restrictive. Any modification or variation can be made in the present invention.

COMPARATIVE EXAMPLE 1

A 2.5 µM nucleotide chain (indicated in the final concentration; the same holds true for the description below), 1 u/µl TdT, 0.2 u/µl UDG, and 1 mM dUTP were mixed in the same way as in Example 1. To this liquid reaction mixture, 1 mM aminooxy biotin was added in advance. 2 mM cobalt chloride was used as an activator for TdT. The liquid reaction mixture was kept at 37° C. for 30 minutes in the presence of a 0.1 M potassium cacodylate buffer solution (pH 7.2).

Figure 5:
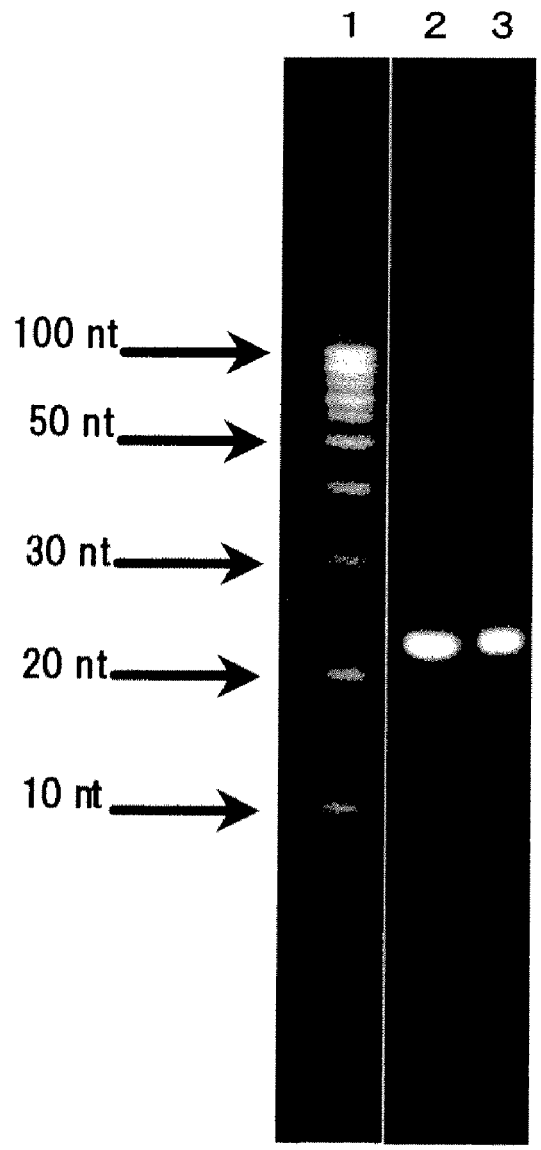
FIG. 5 is electrophoretic patterns on polyacrylamide gel showing the influence of an enzyme activator on the method of modifying a nucleotide chain according to the present invention.

This nucleotide modification process was monitored by 7 M urea-polyacrylamide gel electrophoresis in the same way as in Example 1. The results are shown in FIG. 5.

A lane 1 shows an electrophoretic pattern of the same molecular weight marker as in Example 1. Arrows on the left of the lane 1 respectively represent migration positions of 100-nt, 50-nt, 30-nt, 20-nt, and 10-nt polynucleotide chains.

A lane 2 shows an electrophoretic pattern of an untreated nucleotide chain, and a lane 3 shows an electrophoretic pattern of the treated nucleotide chain.

No difference in electrophoretic mobility is observed between the nucleotide chains shown in the lanes 2 and 3. This demonstrates that the nucleotide chain in the lane 3 was not modified with biotin, that is, the tailing reaction catalyzed by TdT did not occur.

Next, aminooxy biotin was used as a modifier without the addition of the nucleotide chain, the nucleotide to be added, and the enzymes to examine a suitable combination of an activator and a buffer solution. The results are shown in Table 2 below.

TABLE 2

| Formation of insoluble complex with aminooxy biotin | | |
|---|---|---|
| Cobalt chloride | Magnesium chloride | Manganese chloride |
| (+) | (−) | (−) |

(+): Pellets were present.
(−): Pellets were absent.

Neither the potassium cacodylate nor the 4-(2-hydroxyethyl)piperazine-1-ethanesulfonic acid-potassium hydroxide of Example 1 used as a buffer solution produced pellets even in the presence of magnesium chloride or manganese chloride as an activator coexisting with aminooxy biotin. However, these buffer solutions produced brown pellets in the presence of cobalt chloride coexisting therewith. This is probably because the cobalt ion reacts with the amino group in the aminooxy biotin to form an insoluble complex.

This result means that, when a cobalt ion is used as the activator, a functional group such as an aldehyde group is formed at the 3'-terminus of the nucleotide chain, and this nucleotide chain must then be separated from the cobalt ion by ethanol precipitation or other methods. Thus, the process is difficult to shift immediately to the modification reaction of the modifier.

By contrast, when the magnesium or manganese ion is used, insoluble pellets are not formed through reaction with the modifier having —$NH_2$. Therefore, a functional group such as an aldehyde group is formed at the 3'-terminus of the nucleotide chain, and this liquid reaction mixture can then be mixed with the modifier without performing, for example, procedures of collecting the nucleotide chain by ethanol precipitation or replacing the composition of the liquid reaction mixture by gel filtration. Thus, the process can be shifted immediately to the modification reaction.

COMPARATIVE EXAMPLE 2

A nucleotide chain was tailed with dUMPs in the same way as in Example 1 except that various buffer solutions (50 μl in total) containing activators shown below were used.
Buffer solution 1: 50 mM 4-(2-hydroxyethyl)piperazine-1-ethanesulfonic acid-potassium hydroxide buffer solution (pH 7.2) containing 2 mM magnesium chloride (hereinafter, referred to as a magnesium-containing sulfonic acid buffer solution)
Buffer solution 2: 50 mM 4-(2-hydroxyethyl)piperazine-1-ethanesulfonic acid-potassium hydroxide buffer solution (pH 7.2) containing 2 mM manganese chloride (hereinafter, referred to as a manganese-containing sulfonic acid buffer, solution)
Buffer solution 3: 0.1 M potassium cacodylate buffer solution (pH 7.2) containing 2 mM cobalt chloride (hereinafter, referred to as a cobalt-containing cacodylate buffer solution)

Changes in the nucleotide chain in a reaction mixture solution obtained using each buffer solution were monitored over time at 30-minute intervals (30, 60, 90, and 120 minutes) by 7 M urea-polyacrylamide gel electrophoresis in the same way as in Example 1. The results are shown in FIG. 6.

A lane 1 shows an electrophoretic pattern of the same molecular weight marker as in Example 1. Arrows on the left of the lane 1 respectively represent migration positions of 100-nt, 50-nt, 30-nt, 20-nt, and 10-nt polynucleotide chains. A lane 2 shows an electrophoretic pattern of an untreated nucleotide chain.

Lanes 3 to 6 respectively show changes over time (30, 60, 90, and 120 minutes) in the nucleotide chain achieved using the magnesium-containing sulfonic acid buffer solution;
lanes 7 to 10 respectively show changes over time (30, 60, 90, and 120 minutes) in the nucleotide chain achieved using the manganese-containing sulfonic acid buffer solution; and
Lanes 11 to 14 respectively show changes over time (30, 60, 90, and 120 minutes) in the nucleotide chain achieved using the cobalt-containing cacodylate buffer solution.

Figure 6:
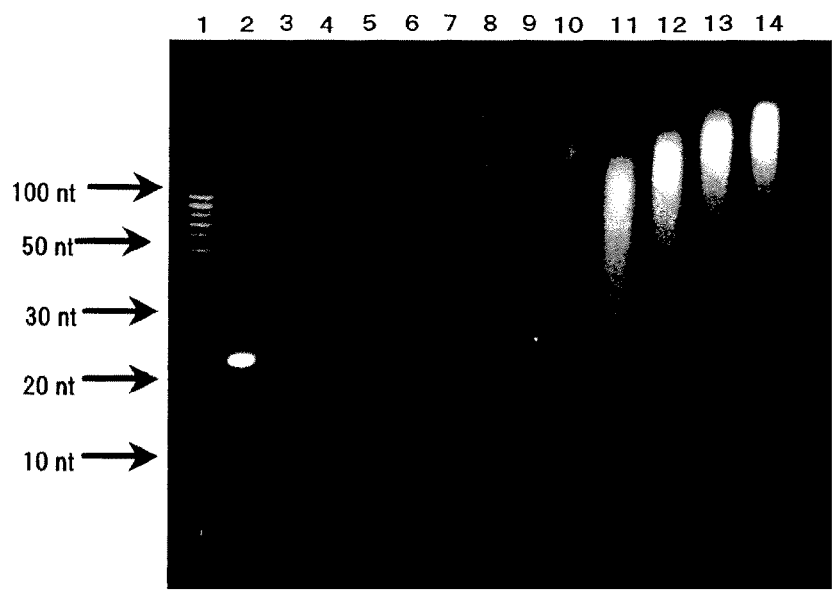
FIG. 6 is electrophoretic patterns on polyacrylamide gel showing the influence of the enzyme activator and a buffer component in a tailing reaction on the method of modifying a nucleotide chain according to the present invention.

As shown in FIG. 6, the tailing reaction efficiency of dUMPs is highest with the use of the cobalt-containing cacodylate buffer solution, followed by the manganese-containing sulfonic acid buffer solution. The lowest tailing reaction efficiency is obtained with the use of the magnesium-containing sulfonic acid buffer solution. This result is consistent with previous reports showing that the cobalt ion-cacodylate buffer solution combination produces highest reaction activity in TdT reaction (e.g., Bollum F J., The Enzymes, vol. 10, p. 145, 1974, Academic Press).

However, the method of the present invention is intended to form a functional group such as an aldehyde group at the 3'-terminus of the nucleotide chain. For this purpose, lower reaction efficiency of TdT results in a smaller amount of substrates for subsequent degradation reaction by UDG and is therefore rather preferable. This is because the degradation reaction through which the added nucleotide (e.g., dUMPs) is degraded is facilitated by preventing the nucleotide from being excessively added to the nucleotide chain.

Therefore, preferably, the cobalt ion-cacodylate buffer solution combination is avoided from the viewpoint of the reaction efficiency of TdT and from the viewpoint that the cobalt ion is responsible for precipitation of the modifier and that the cacodylate itself is an arsenic compound.

Thus, when TdT is used as the enzyme catalyzing the addition reaction, a divalent metal cation other than a cobalt ion, for example, a manganese or magnesium ion, is preferably used as the activator thereof. As a result, the precipitation of the modifier can be prevented. Moreover, a buffer component which moderates the reaction activity of TdT, for example, 4-(2-hydroxyethyl)piperazine-1-ethanesulfonic acid, is preferably used. Alternatively, a Good's buffer (e.g., 2-morpholinoethanesulfonic acid) or 3,3-dimethylglutaric acid may also be used.

These buffers have no amino group in the chemical structures and can therefore circumvent modification reaction inhibition caused by a buffer having —$NH_2$, such as 2-amino-2-hydroxymethyl-1,3-propanediol (commonly called Tris) generally used as a buffer.

In these Examples, the combination of an activator having a less favorable ability to activate the enzyme TdT and a buffer solution component which moderates reaction progress has been illustrated by taking, as an example, the tailing reaction with dUMPs. However, the combination of the buffer solution component and the TdT activator used in the present invention is not limited to this combination. In the tailing reaction of 2'-deoxynucleotide 5'-monophosphate having the base shown in Table 1, an appropriate combination of a buffer solution component which moderates the progress of the tailing reaction and a TdT activator other than a cobalt ion can be adopted.

Some nucleotide chains acquired by chemical synthesis or through a replication reaction form, in the sequences thereof, a nucleotide having the base shown in Table 1 which is absent in natural nucleotides. For example, when plural guanine or cytosine bases are present in the base sequence of a nucleotide chain during a replication reaction thereof, incorporation of a nucleotide having guanine through the replication reaction is responsible for reduction in replication efficiency. In this case, a nucleotide having hypoxanthine instead of guanine is used (e.g., Nucleic Acids Res., vol. 21, p. 4427, 1993). The nucleotide chain thus acquired through the replication reaction has hypoxanthine in the sequence thereof. Thus, the nucleotide chain to be modified is degraded through the degradation reaction, when tailed with the nucleotide having hypoxanthine illustrated in the method of modifying a nucleotide chain according to the present invention. In such a case, a nucleotide having a base other than hypoxanthine may be selected appropriately for the tailing reaction. The DNA glycosylase or DNA repair enzyme used in the subsequent degradation reaction is specific to the nucleotide having the base serving as a substrate for the degrading enzyme. Therefore, the degradation of the nucleotide chain to be modified can be circumvented.

INDUSTRIAL APPLICABILITY

According to a method of modifying a nucleotide chain according to the present invention, the 3'-terminus of a nucleotide chain to be modified can be modified with any modifier quantitatively, stably, and conveniently in a short time, with the original state of the nucleotide chain maintained, regardless of a nucleotide chain length. Thus, the method of modifying a nucleotide chain according to the present invention is useful in, for example, gene analysis that requires nucleotide chain labeling, immobilization, etc.

The invention claimed is:

1. A method of modifying a nucleotide chain, comprising:
providing an initial DNA nucleotide chain having at least two consecutive 2'-deoxyuridine 5'-monophosphate at the 3' terminus;
preparing a reaction mixture solution comprising: a buffer solution, the initial DNA nucleotide chain, terminal deoxynucleotidyl transferase, a divalent metal cation other than a cobalt ion, and a buffer component selected from the group consisting of 4-(2-hydroxyethyl)piperazine-1-ethanesulfonic acid, 2 morpholinoethanesulfonic acid, and 3,3-dimethylglutaric acid;
adding uracil-DNA glycosylase to the reaction mixture solution to degrade the at least two 2'-deoxyuridine 5'-monophosphate at the 3'-terminus of the nucleotide chain, thereby forming an aldehyde group capable of binding to a modifier having an —NH$_2$ group; and
modifying directly the 3'-terminus of the nucleotide chain having the aldehyde group, with a modifier having an —NH$_2$ group.

2. The method of modifying a nucleotide chain according to claim 1, wherein the divalent metal cation is a manganese or magnesium ion.

3. The method of modifying a nucleotide chain according to claim 1, wherein the modifier having an —NH$_2$ group is a substance for labeling and/or conjugating the nucleotide chain.

4. The method of modifying a nucleotide chain according to claim 1, wherein the modifier having an —NH$_2$ group is a substance via which the nucleotide chain is bound to a substrate.

5. The method of modifying a nucleotide chain according to claim 4, wherein the having an —NH$_2$ group further comprises a thiol group.

6. The method of modifying a nucleotide chain according to claim 4, wherein the having an —NH$_2$ group further comprises an alkoxysilyl group that is hydrolyzable to a silanol group.

7. The method of modifying a nucleotide chain according to claim 1, wherein the reaction mixture solution is heat-treated or alkali-treated after the step of adding but before the step of modifying.

* * * * *

SEQUENCE LISTING

```
<160> NUMBER OF SEQ ID NOS: 1

<210> SEQ ID NO 1
<211> LENGTH: 25
<212> TYPE: DNA
<213> ORGANISM: Artificial
<220> FEATURE:
<223> OTHER INFORMATION: chemical synthesized oligodeoxynucleotide
<220> FEATURE:
<221> NAME/KEY: misc_feature
<223> OTHER INFORMATION: complementary sequence for human adult myosin
      heavy chain 1 in the region 5810 to 5786
<300> PUBLICATION INFORMATION:
<308> DATABASE ACCESSION NUMBER: NM_005963
<309> DATABASE ENTRY DATE: 2004-02-02
<313> RELEVANT RESIDUES IN SEQ ID NO: (5786)..(5810)

<400> SEQUENCE: 1
cttatgattt tgtgtgaac ctccc                                            25
```